United States Patent

Hirayama et al.

[11] Patent Number: 6,121,617
[45] Date of Patent: Sep. 19, 2000

[54] INFRARED GAS ANALYZER

[75] Inventors: Noritomo Hirayama; Satoru Sakaue; Masahiro Uno; Yosheyuki Sekine, all of Tokyo, Japan

[73] Assignee: Fuji Electric Co., Ltd., Kawasaki, Japan

[21] Appl. No.: 09/026,514

[22] Filed: Feb. 19, 1998

[30] Foreign Application Priority Data

Feb. 26, 1997 [JP] Japan .................................... 9-042713

[51] Int. Cl.$^7$ .................................................. G01N 21/35
[52] U.S. Cl. .......................................... 250/343; 250/351
[58] Field of Search ..................................... 250/343, 351

[56] References Cited

U.S. PATENT DOCUMENTS

| 4,749,276 | 6/1988 | Bragg et al. | 356/246 |
| 5,428,222 | 6/1995 | Alexay | 250/343 |
| 5,734,165 | 3/1998 | Unal et al. | 250/338.1 |

FOREIGN PATENT DOCUMENTS 61-28843  2/1986  Japan ..................... 250/343

*Primary Examiner*—Constantine Hannaher
*Attorney, Agent, or Firm*—Kanesaka & Takeuchi

[57] ABSTRACT

An infrared gas analyzer is formed of a source of infrared rays for emitting infrared flux; an infrared flux interrupting device for chopping the emitted infrared flux from the source of the infrared rays; a condensing optical system for obtaining a predetermined solid angle in the emitted infrared flux to thereby form a condensed flux; and a multi-reflection cell disposed at an outlet of the condensing optical system, to which the condensed flux is supplied and a gas to be measured is fed. The multi-reflection cell has a multi-reflection optical system formed of a plurality of concave mirrors. The analyzer also includes an infrared level detector for detecting an amount of infrared rays with a wavelength band absorbed by a component gas to be analyzed and contained in the infrared rays emitted by the multi-reflection cell. At least the condensing optical system, multi-reflection cell and infrared level detector are accurately positioned by using as a reference a position of the condensing optical system at which the condensed flux is emitted, and are coupled tightly at coupling positions without an air-flowing layer. Accordingly, the infrared gas analyzer can be made small to detect and analyze a low density component gas and for an explosion-proof environment.

11 Claims, 9 Drawing Sheets

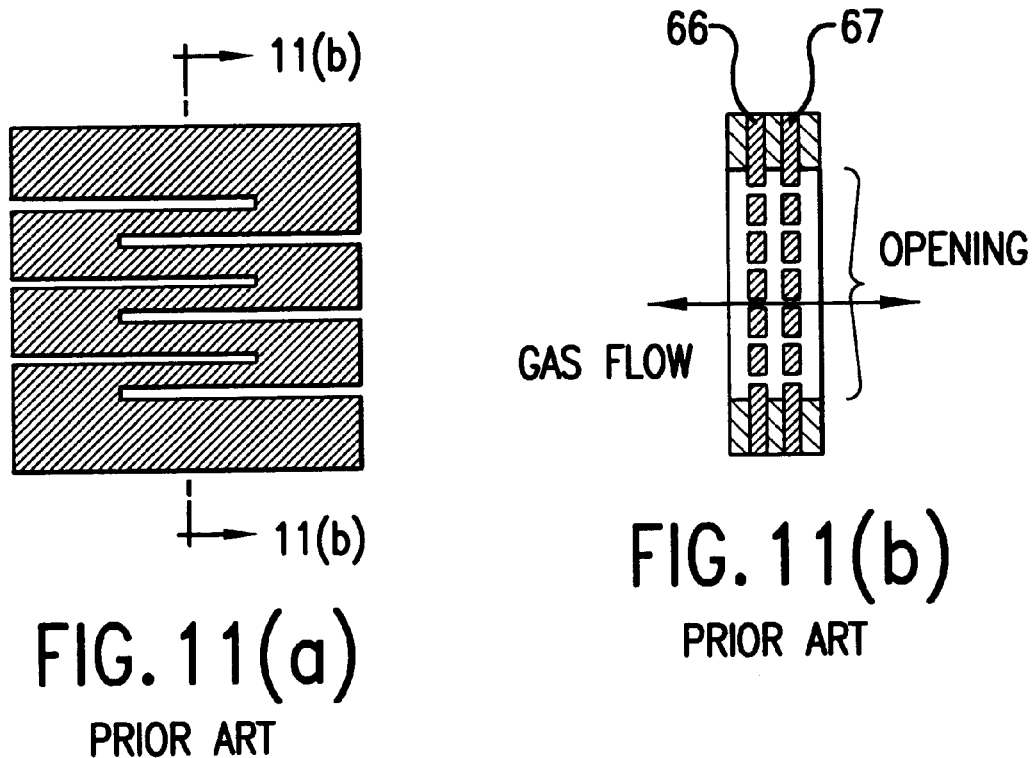
FIG. 11(a)
PRIOR ART
FIG. 11(b)
PRIOR ART
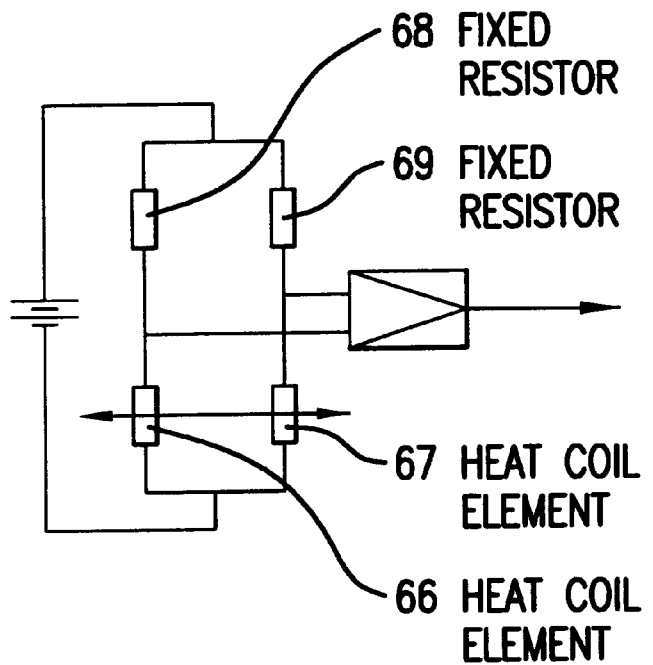
FIG. 11(c)
PRIOR ART

INFRARED GAS ANALYZER

BACKGROUND OF THE INVENTION AND RELATED ART STATEMENT

The present invention relates to an infrared gas analyzer for qualitatively or quantitatively analyzing a component gas to be analyzed and contained in a gas to be measured by detecting an amount of infrared rays absorbed.

An infrared gas analyzer irradiates a gas to be measured with infrared rays to measure an amount of infrared rays with a particular wavelength region absorbed by a component gas to be analyzed and contained in the gas to be measured in order to qualitatively or quantitatively analyze the components of the gas to be measured based on the amount of infrared rays absorbed. This method is commonly used because it generally offers good selectivity and high measurement sensitivity.

FIG. 10 is a cross sectional view showing a structure of an example of a conventional single-beam infrared gas analyzer. A source of infrared rays 3 has an emitter such as a nichrome wire, and the emitter is supplied with electricity for heating to emit infrared rays. The infrared flux emitted from the infrared source 3 is changed into discontinuous or intermittent light by a rotating chopper 2 driven by a motor 1 and is supplied to a measuring cell 5 as a measured beam 4. The measuring cell 5 is formed like a cylinder with infrared transmission windows 51 and 52 attached at both ends, and the beam is inputted and outputted through the windows. In addition, the measuring cell 5 includes an inlet tube 53 and a discharge tube 54 for introducing and discharging a gas to be measured. In the measuring cell 5, the measuring beam 4 is subjected to absorption depending on the concentration of a component gas in the gas to be measured and introduced into the measuring cell 5. The measuring beam 4 passing through the measuring cell 5 is ejected to a detector 6 that detects infrared rays of a particular wavelength band.

The detector 6 has a first and second expansion chambers 63 and 64 in series with the direction in which the measuring beam 4 advances, so that the measuring beam 4 passing through the measuring cell 5 enters through an infrared transmission window 61 the first expansion chamber 63 which is the front chamber. The measuring beam 4 passing through the first expansion window 63 further passes through an infrared transmission window 62 to the second expansion chamber 64 that is a rear chamber. The same gas as the component gas to be analyzed is sealed in both expansion chambers 63 and 64. Infrared rays with wavelength components having a high absorption coefficient in terms of the wavelength-infrared rays absorption characteristic of the sealed gas are mostly absorbed in the first expansion chamber 63, which is the front chamber, while the wavelength components that have not been absorbed in the first expansion chamber, that is, those having medium absorption coefficients, are mainly absorbed in the second expansion chamber 64, which is the rear chamber.

A temperature of the sealed gas increases depending on the amount of infrared rays absorbed, to thereby increase the pressures of the expansion chambers 63 and 64. The sealed gas flows in a gas passage 65 based on the pressure differential between the expansion chambers 63 and 64 which is caused by the difference in the amount of infrared rays absorbed, that is, the concentration of the analyze-component gas in the gas to be measured. The concentration of the analyze-component gas in the gas to be measured can be detected by measuring the flow rate.

FIG. 11(a) is a plan view of heating coil elements 66 and 67 for detecting the gas flow rate. FIG. 11(b) is a cross sectional view taken along line 11(b)—11(b) in FIG. 11(a). FIG. 11(c) is a circuit diagram of a detection circuit.

The heating coil elements 66 and 67 are made of an electric conductor in which the resistance value sensitively varies with a temperature, that is, one having a high resistance temperature coefficient (for example, nickel). In FIGS. 11(a)–11(c), a rectangular foil of nickel is etched from both sides so as to be formed into a zigzag resistor as shown in FIG. 11(a), and two such resistors are disposed adjacent to each other and integrally fixed to each other at their outer circumferences as shown in FIG. 11(b). The center areas of the resistors form an opening through which a gas can flow. Such a pair of heating coil elements 66 and 67 is disposed in the gas passage 65 in the longitudinal direction relative to the gas flow.

The pair of heating coil elements 66 and 67 is combined with a pair of fixed resistors 68 and 69 so as to constitute a Wheatstone bridge circuit as shown in FIG. 11(c), and is heated by a current provided by a power supply connected to the Wheatstone bridge to increase a temperature above the ambient temperature. In addition, due to their relative proximity, the heating coil elements 66 and 67 thermally affect each other.

When there is no difference in pressure between the first and second expansion chambers 63 and 64, since the gas does not flow, temperatures of the two heating coil elements are balanced with the ambient temperature. If there is a difference in pressure between the first and second expansion chambers 63 and 64 and the gas flows through the gas passage 65, a temperature of the heating coil element on the upstream side of the gas flow is decreased by direct contact with the gas flow, while the downstream heating coil element contacts the gas flow heated by the upstream heating coil element and thus becomes hotter than the upstream element. In this manner, the temperatures of the heating coil elements 66 and 67 vary with the intensity of the gas flow through the gas passage 65, that is, the difference in pressure between the first and second expansion chambers 63 and 64. This variation is detected by the output from the Wheatstone bridge circuit. Since this output is in proportion to the concentration of the analyze-component gas contained in the gas to be measured, the concentration of the analyze-component gas can be measured by using the output from the Wheatstone bridge circuit.

If the infrared gas analyzer of the structure shown in FIG. 10 is used to detect a low density analyze-component gas contained in the gas to be measured, since a smaller amount of infrared rays is absorbed, a sufficient output can not be obtained. The required output has thus been obtained by increasing the length of the measuring cell 5 and/or the radiant intensity of infrared rays from the infrared source. This method, however, has the following problems.

First, the content volume of the measuring cell 5 increases along with the increase of the length of the cell. When the content volume increases, an amount of gas to be measured required for analysis increases to prevent trace levels of gas from being analyzed; time required to substitute the gas to be measured in the measuring cell 5 increases, to thereby delay the response; required capacities of a pump apparatus and preprocessor for removing dust and moisture in the gas to be measured increase, leading to greater physical sizes and costs for these devices; and the resulting increase in size of such an apparatus leads to an increase in the thermal capacity, thus increasing the time required for warming up the apparatus. In addition to these problems, a more serious problem is that if the analyzer is used in an environment involving petroleum or petrochemical processes, which require an explosion-proof structure, the size, weight and cost of the equipment become huge. Since the infrared source used in this type of the infrared gas analyzer is also a source of heat, the light source must at least be housed in a pressurized container in order to be used in an explosion-proof environment as described above. Since, however, optically transparent windows required to obtain infrared rays have a low pressure resistance, the entire infrared gas analyzer body including the measuring cell and the infrared detector must be housed in a pressurized container, so that the reduction of the size of the components such as the measuring cell and the infrared detector is an important practical matter.

Second, an increase in the radiant intensity of infrared rays from the infrared source increases the calorific value of the infrared source, so that time required to stabilize its temperature increases, thereby increasing the time required for warmup operations.

Third, the conventional infrared gas analyzer has an outside-air-flowing layer in an optical path extending from the infrared source to the infrared detector. When a low density component gas to be analyzed is detected and if the component gas having an absorption band in the same wavelength region as in the component gas to be analyzed is present in air and its concentration varies, then not only the measured beam 4 is absorbed in the measuring cell 5 but the infrared rays in the absorption band of the analyzed-component gas are also absorbed in that part of the optical path extending from the infrared source to the infrared detector, which passes through the outside layer. Thus, the measurement sensitivity decreases to degrade the measurement accuracy, preventing low concentrations from being detected easily. One example is the effect of carbon dioxide ($Co_2$) in air in the measurement of the concentration of carbon monoxide (CO).

A multi-reflection measuring cell originated by White (hereafter referred to as a "White cell") has been used to solve the first of the above problems. This cell has a structure such as that shown in FIG. 12. In this structure, a condensed beam of infrared rays is applied on a multi-reflection optical system and travels or passes back and forth within a small space to establish a long optical path. It is described in the following documents and is publicly known.

(1) J. U. White, J. Opt. Soc. Am., vol. 32, 285 (1942)

(2) J. U. White, N. L. Alpert, A. D. DeBell, J. Opt. Soc. Am., vol. 45, 154 (1955)

(3) P. Hannan, Opt. Engineering, vol. 28, 1180 (1989)

The structure of the White cell 7 is described in detail with reference to FIG. 12.

A central concave mirror 75, an input image-forming mirror 76, and an output image-forming mirror 77 are concave mirrors with the same radius of curvature and disposed in such a way that the distance between opposite reflecting surfaces is equal to the radius of curvature. An incident window 71 used to introduce an incident beam 41 is provided adjacent to the central concave mirror 75 as a slit or a small hole, while an input image-forming mirror 76 is disposed opposite to the incident window 71 such that it forms on the central concave mirror 75 an image of the incident beam 41 through the incident window 71. The beam reflected from the central concave mirror 75 is reflected by the output image-forming mirror 77 disposed next to the input image-forming mirror 76 and again forms an image on the central concave mirror 75. After such reflective image forming is repeated for the required number of times, the beam reflected by the output image-forming mirror 77 is emitted through an emitting window 72 disposed adjacent to the central concave mirror 75 and opposite to the incident mirror 71. The incident beam 41 emitted into the White cell 7 is a condensed beam that enables a reflected image to be formed many times within the White cell 7.

In FIG. 12, the incident beam 41 is reflected by each of the input and output image-forming mirrors 76 and 77 four times and by the central concave mirror 75 seven times in the alphabetical order of (a) to (g), and travels back and forth eight times between the concave mirrors before being emitted as an emitted beam 42.

Thus, due to its ability to substantially reduce the content volume of the measuring cell, the White cell 7 is very effective means for solving the first problem. The White cell, however, does not serve to sufficiently reduce the size of the conventional infrared gas analyzer that is a simple combination of the infrared source 3, the White cell 7 as the measuring cell, and the infrared detector, and therefore requires a relatively large area in between these elements. The reason for this is described below.

Optical components including several concave mirrors are used for the White cell 7 and a condensing optical system in the preceding stage, and must be disposed and oriented very accurately to achieve the required accuracy of their optical axes. This accuracy can not be maintained easily due to the thermal expansion of the members caused by radiant heat from the infrared source 3, and as a result, a predetermined amount of light or a required optical path length may not be obtained. Consequently, the analyzer must have a structure such that the optical system can be adjusted. That is, it is difficult to integrally form the analyzer. Although an example of integration of the measuring cell and the infrared detector has been shown in a catalog from DASIBI, no conventional analyzers are integrally formed up to the periphery of the infrared source.

With respect to the second problem, the infrared source 3 must provide a certain amount of light to obtain the required output level. While this requirement is met, the size of the analyzer must be reduced. Of course, the size of the infrared source 3 is desirably minimized to obtain good results including increased use efficiency, but to do this, a temperature of the emitting section of the source must be increased. In this case, the radiant heat also increases to cause an increase in temperature and thermal expansion, both of which are more serious problems.

Solutions to the third problem are described below.

One method is to form the entire infrared gas analyzer such that a space in the optical path extending from the infrared source 3 to the infrared detector 6 through which the outside air can pass is minimized, while keeping the structure of the infrared gas analyzer unchanged.

A second method is to seal the entire infrared gas analyzer in an atmosphere filled with a gas that does not absorb infrared rays, for example, a nitrogen gas.

A third method is to increase the substantial length of the measuring cell up to a value at which the effects of the outside air portion are negligible.

However, the first method is insufficient, and the second method results in a complicated configuration and thus an increased size due to the addition of a structure that must enclose the entire analyzer. The third method is inconsistent with the reduction of the size of the device.

It is an object of this invention to solve the above problems of the conventional infrared gas analyzers and to provide a small infrared gas analyzer that can detect and analyze a low density component gas to be analyzed and that can provide an explosion-proof environment.

SUMMARY OF THE INVENTION

The first aspect of the invention resides in an infrared gas analyzer comprising a source of infrared rays for emitting infrared rays or flux; infrared flux interrupting means for chopping the emitted infrared flux; a condensing optical system for obtaining a predetermined solid angle in the emitted infrared flux to thereby form a condensed flux; a multiple reflection cell disposed at an outlet of the condensing optical system in which a gas to be measured is fed, and having a built-in multiple reflection optical system composed of a plurality of, e.g. three, concave mirrors; and infrared level detection means disposed at an infrared emitting section of the multiple reflection cell for detecting an amount of infrared rays with a wavelength band absorbed by a component gas to be analyzed and contained in the infrared rays emitted from the multiple reflection cell, wherein at least the condensing optical system, multi-reflection cell and infrared amount detecting means are accurately positioned by using as a reference a position of the condensing optical system at which the condensed flux is emitted, and are coupled tightly at coupling positions without an airflowing layer.

Since the parts are tightly and accurately positioned and coupled together without the outside-air-flowing layer, the entire analyzer can be miniaturized and thermally integrally formed to provide an optical path for the infrared flux rays and to enable the multiple reflection cell to function effectively, thereby enabling a low density component gas to be detected and analyzed.

According to a second aspect of the invention, the condensing optical system and the infrared level detector are contacted with each other to maintain a uniform temperature. The condensing optical system that is the first stage for the condensed flux and the infrared amount detection means that is the final stage for the condensed flux contact with each other so as to maintain a uniform temperature in the entire analyzer.

According to a third aspect of the invention, the analyzer includes as an infrared radiating section of the infrared source an emitter comprising molybdenum silicide or a composite ceramic containing molybdenum silicide. The emitter formed of such a material has a very high operating temperature, thereby enabling the analyzer to be miniaturized.

According to a fourth aspect of the invention, a holding section of the infrared radiating section of the infrared source includes a hermetic structure. This hermetic structure enables the emitter to be positioned accurately.

According to a fifth aspect of the invention, the infrared radiating section of the infrared source is shaped by folding a ribbon with a rectangular cross section. The thickness of the ribbon and the interval between the folded parts of the ribbon are almost equal, and the direction perpendicular to a main emitting surface of the infrared radiating section is tilted relative to the incident axis of the condensing optical system. Since the direction perpendicular to the main emitting surface of the infrared radiating section is tilted relative to the incident axis of the condensing optical system, not only infrared rays from the main radiating surface of the infrared radiating section but also infrared rays from the sides can be used to effectively increase the infrared radiating area.

According to a sixth aspect of the invention, the infrared flux interrupting means is shaped by cutting a part of a cylinder, and a shaft is mounted at the center of one end of the cylinder in such a way that the shaft can be rotated. The infrared flux interrupting means covers the infrared radiating section of the infrared source and rotates around the infrared radiating section. Since the infrared flux interrupting means is formed to rotate around the infrared radiating section, it can be substantially miniaturized as compared to the conventional disc methods.

According to a seventh aspect of the invention, a specific component gas is sealed inside the condensing optical system, and the condensing optical system also functions as a gas filter. The gas filter can eliminate the effects of an interfering-component gas.

According to an eighth aspect of the invention, a photo detector is disposed at a position at which a part of the infrared flux from the infrared source chopped by the infrared flux interrupting means can be detected. This photo detector can detect the conditions of the infrared source and infrared flux interrupting means.

According to a ninth aspect of the invention, a rotational condition of the infrared flux interrupting means is detected by using a chopping frequency of the infrared source detected by the photo detector. This enables the detection of an error in the rotation of the infrared flux interrupting means, for example, its stoppage.

According to a tenth aspect of the invention, an amount of light from the infrared source is calculated from the output from the photo detector to detect the condition of changes in the characteristics of the infrared source while correcting the variation of voltages applied to the infrared source and infrared amount detector in order to adjust the sensitivity of an infrared level detector. The condition of changes in the characteristics of the infrared source and the variation of a power supply are compensated for to significantly improve the stability of the sensitivity of the infrared level detection means.

According to an eleventh aspect of the invention, the output from the photo detector is used as a reference signal for a processing circuit for the infrared amount detector. This enables an accurate reference signal to be obtained, thus significantly improving the accuracy of processing executed by the processing circuit for the infrared amount detection means.

BRIEF DESCRIPTION OF THE DRAWINGS

FIG. 11(a) is a cross sectional view of heating coil elements used in an infrared detector viewed from above;

FIG. 11(b) is a cross sectional view of the heating coil elements viewed from the side;

FIG. 11(c) shows a detection circuit thereof;

DETAILED DESCRIPTION OF PREFERRED EMBODIMENTS

Figure 1:
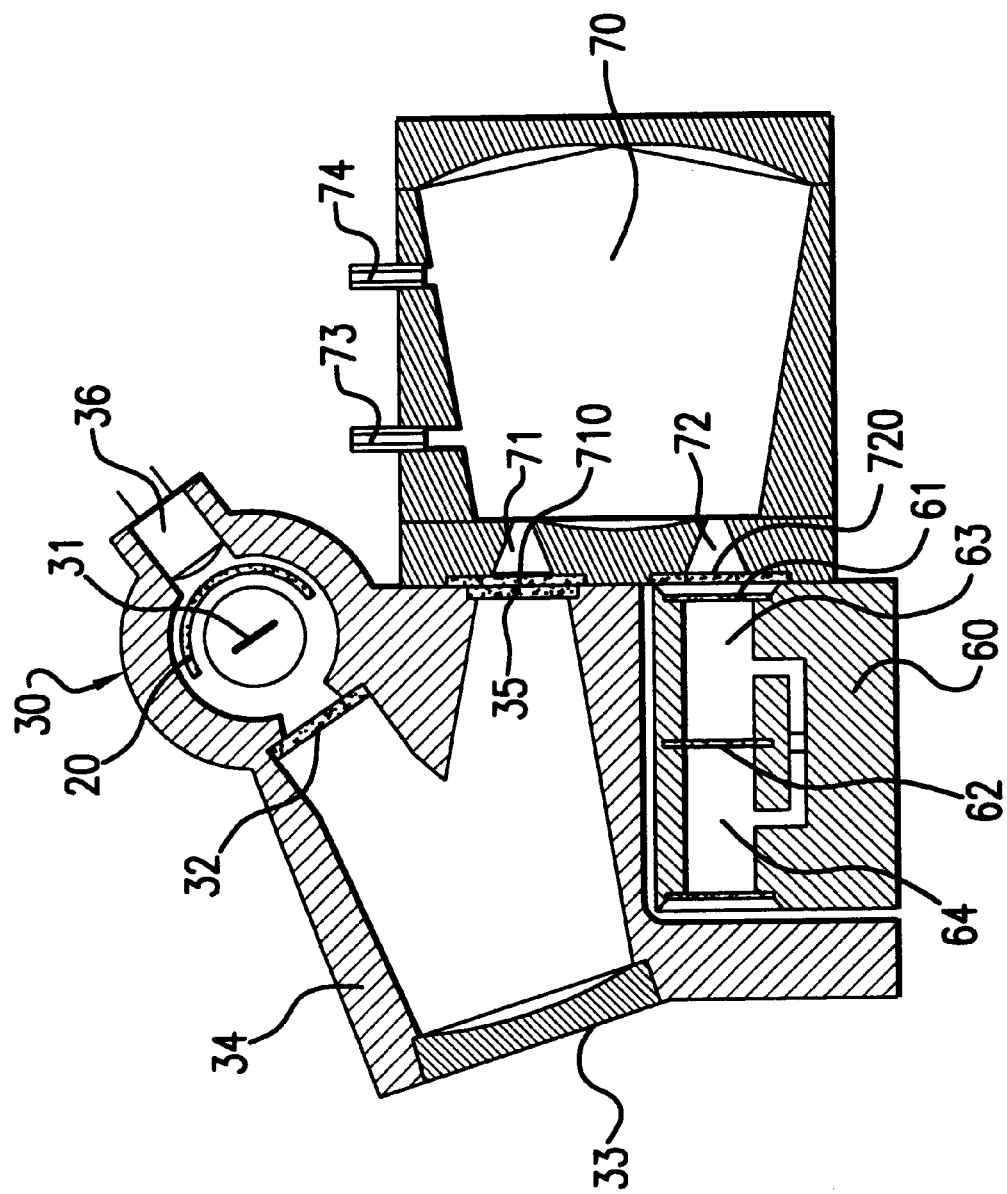
FIG. 1 is a cross sectional view showing a structure of a first embodiment of an infrared gas analyzer according to the invention.

The basic structure of this invention is to make each component compact while minimizing the space required to connect the components and to thermally integrally form the entire analyzer without an outside-air-flowing layer in the connection. By integrally forming the entire analyzer compact, the difference in temperature among the components caused by heat from the source of infrared rays can be minimized. This substantially reduces the associated distortion and thus provides a much smaller infrared gas analyzer than the conventional ones.

This invention is described in detail with reference to specific embodiments. The components having the same functions as in the prior art have the same reference numerals.

FIG. 1 is a cross sectional view showing a structure of a first embodiment of an infrared gas analyzer according to this invention. This is a single-beam infrared gas analyzer. In a source of infrared rays 30, an emitter section 31 consisting of a conductive ceramic and a cylindrical rotating chopper 20 which surrounds the emitter section, rotates around it and has a notch in a part thereof for interrupting an infrared flux, is housed in a predetermined position of a stainless steel enclosure 34. This enclosure also functions as an enclosure for a condensing optical system for condensing the flux emitted from the emitter section 31. An infrared transmission window 32 consisting of an infrared transmission material such as calcium fluoride for obtaining an infrared flux from the emitter section 31 and maintaining the air-tightness of the inside of the condensing optical system is attached by an adhesive to a flux capture section of the enclosure 34, in which the emitter section 31 is housed. A photodiode 36 is disposed in the periphery of the enclosure 34 surrounding the emitter section 31 and opposite to the infrared transmission window 32 as a photo detector to detect an amount of light from the emitter section 31 which is chopped by the rotating chopper 20.

A concave condensing mirror 33 that cedenses an obtained infrared flux is attached by an adhesive to the enclosure 34 opposite to the infrared transmission window 32. An infrared flux is condensed at a position with a predetermined angle relative to the source by the concave condensing mirror 33. An opening used to obtain the condensed flux is provided at the position of the enclosure 34 corresponding to the condensing position, and an infrared transmission window 35 is also attached by an adhesive to this position to maintain the air-tightness of the inside of the condensing optical system. The concave condensing mirror 33 is made of aluminum and has an ion plating layer of gold formed on its reflection surface to improve the infrared reflectance.

An infrared incident window 71 (incident window in FIG. 1) of a White cell 70 is disposed to be adhered to the infrared transmission window 35 provided on the enclosure 34 in order to feed the infrared flux to the inside of the White cell 70. An infrared transmission window 710 of calcium fluoride is attached to the infrared incident window 71 by an adhesive to make the window 71 air-tightly, and the infrared transmission windows 35 and 710 are coupled together in such a way that a sufficiently thin outside air layer is formed between them. An inlet tube 73 for introducing a gas to be measured and a discharge tube 74 for discharging the gas are attached to the White cell 70. Three concave mirrors, which have an equal radius of curvature, are disposed in the White cell 70 so that the infrared flux from the incident window 71 is multiply reflected among the three concave mirrors and then emitted to the infrared detector (detector in FIG. 1) 60 through an emitting window 72. An infrared transmission window 720 is attached to the emitting window 72 to make the window 72 air-tightly.

The White cell 70 is composed of an aluminum portion having the incident and emitting windows 71 and 72, and one concave mirror; a stainless steel pipe portion including the introduction and discharge tubes 73 and 74; and an aluminum portion having two concave mirrors. The White cell is positioned by pins (not shown) and integrated with the analyzer by using screws. An ion plating layer of gold is formed on the surface of each of the three concave mirrors as in the concave condensing mirror 33. The stainless pipe portion is produced by using a wax pattern casting method (lost wax process).

The infrared transmission window 61 of the infrared detector 60 is disposed and adhered to the emitting window 72 of the White cell 70 so that the infrared flux enters the infrared detector 60 through the window 61. The infrared detector 60 outputs an amount of incident infrared flux absorbed in the White cell 70, that is, an output corresponding to the concentration of the component gas to be analyzed. The infrared transmission window 720 of the White cell 70 and the infrared transmission window 61 of the infrared detector 60 are coupled together in such a way that a sufficiently thin outside air layer is formed between them.

The enclosure 34 and the White cell 70 are coupled together by using screws, as are the White cell 70 and the infrared detector 60. In addition, the infrared detector 60 is disposed and fitted under the enclosure 34 of the condensing optical system. Although a gap is shown between the detector 60 and the enclosure 34 in FIG. 1, they are actually adhered to each other. Thus, the entire infrared gas analyzer is shaped to be compact and thermally integrated to facilitate the maintenance of a uniform temperature.

The overall configuration has been described generally. Each component will now be described in detail.

Figure 2:
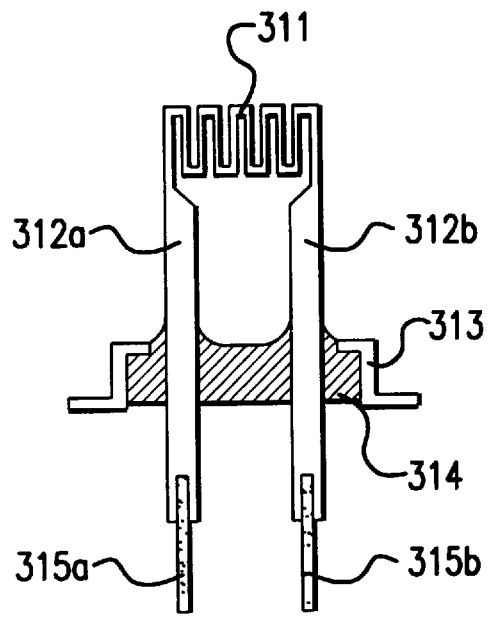
FIG. 2 is a cross sectional view showing a structure of an emitter section of an infrared source according to the first embodiment.

The emitter section 31 of the infrared source 30 will be described first. FIG. 2 is a cross sectional view showing the structure of the emitter section 31. The emitter section 31 comprises a very small ceramic emitter element 331 consisting of 2-molybdenum silicide or a composite material of 2-molybdenum silicide and silicon carbide or molybdenum boride. By way of an example, the size of a zigzag portion that emits light is 5×3 mm. The emitter element 311 can be heated up to 1,200–1,500° C. as compared to 700–800° C. available in the conventional infrared source. This substantially increases the density of the emitted infrared rays, so that the size of the analyzer can be reduced. In addition, since the emitter element 311 can be formed by, for example, electric-discharge machining a sheet material, the analyzer can be miniaturized in terms of machining technology.

Wide linear lead sections 312a and 312b of the emitter element 311 are combined with a hermetic metal member 313 consisting of covar, and a powder-glass molded material that has been press molded to become a sealing material 314 when heated. The combined structure is accurately positioned and set in a jig and then heated to form a hermetic structure. Thus, an emitting unit of the emitter section 31 can be accurately positioned relative to the condensing optical system and can be maintained air-tightly as required.

When the size of the zigzag portion is 5×3mm, the emitter element 311 consumes about 10 W of power.

Figure 3A:
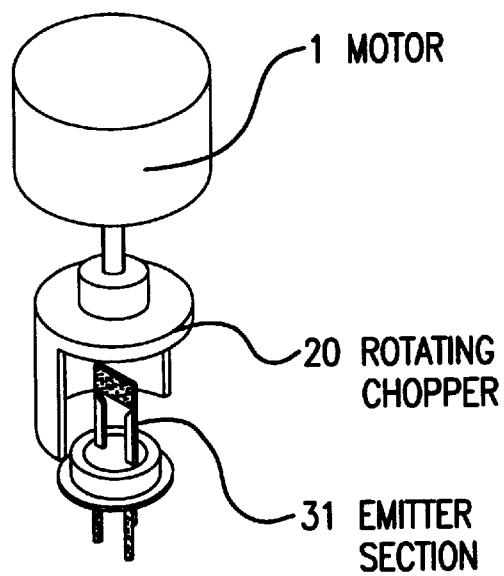
FIG. 3(a) is a perspective view showing a locational relationship between the overall configuration of the rotating chopper and the emitter section in the first embodiment.
Figure 3B:
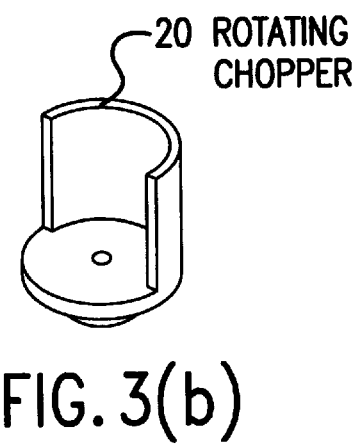
FIG. 3(b) is a perspective view of the rotating chopper.
Figure 3C:
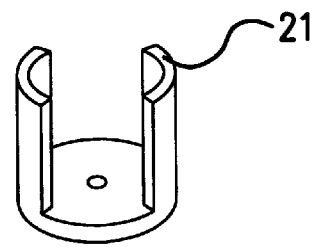
FIG. 3(c) is a perspective view of another rotating chopper.

The infrared flux interrupting means is described with reference to FIGS. 3(a)–3(c). FIG. 3(a) is a perspective view showing the overall configuration and FIGS. 3(b) and 3(c) are perspective views showing two examples of the rotating chopper. The rotating chopper 20 is made of stainless steel and is formed by vertically dividing a cylinder into two and attaching a disc to one end such that the axis of a drive motor 1 can be coupled to the center of the disc. Since the half of the cylinder rotates around the emitter section 31 to interrupt the infrared flux, the infrared flux emitted to the condensing optical system becomes a chopped or discontinuous light with the same frequency as the number of rotation of the motor 1. The rotating chopper 21 shaped as shown in FIG. 3(c) is obtained by vertically dividing a cylinder into four in which two of them oppose to each other, and the emitted infrared flux becomes a discontinuous light with a frequency twice as large as the number of rotation of the motor 1. The rotating chopper 20 or 21 of such a structure requires a much smaller space than the conventional disc-shaped rotating chopper 2.

Next, the purpose of the photodiode 36 will be described. The photodiode 36, acting as a photo detector to detect an amount of light from the emitter section 31 that is chopped by the rotating chopper 20, detects changes in the amount of light emitted from the emitter element 311 based on its output level in order to monitor whether or not the emitter element 311 is degraded, and to output a signal for adjusting the output from the infrared amount detection means. It can also monitor the rotational stability or stoppage of the motor 1 based on the frequency of a detected signal in order to provide a reference signal to a processing circuit for the infrared level detection means.

Since whether or not the emitter element 311 or the motor 1 is degraded can be monitored based on the output from the photodiode 36, their replacement periods can be determined appropriately. In addition, a detected change in the amount of light emitted from the emitter element 311 can be compensated by using the variation of voltages applied to the infrared source and infrared level detection means in order to adjust the sensitivity of the infrared amount detection means, to thereby significantly reduce the effects of that change. It can also provide a reference signal to a processing circuit for adjusting synchronism to obtain a signal component from an output waveform with a bad S/N ratio in a small output signal.

As described above, the photodiode 36 is effective in improving the accuracy of the infrared gas analyzer to improve its reliability.

Figure 4A:
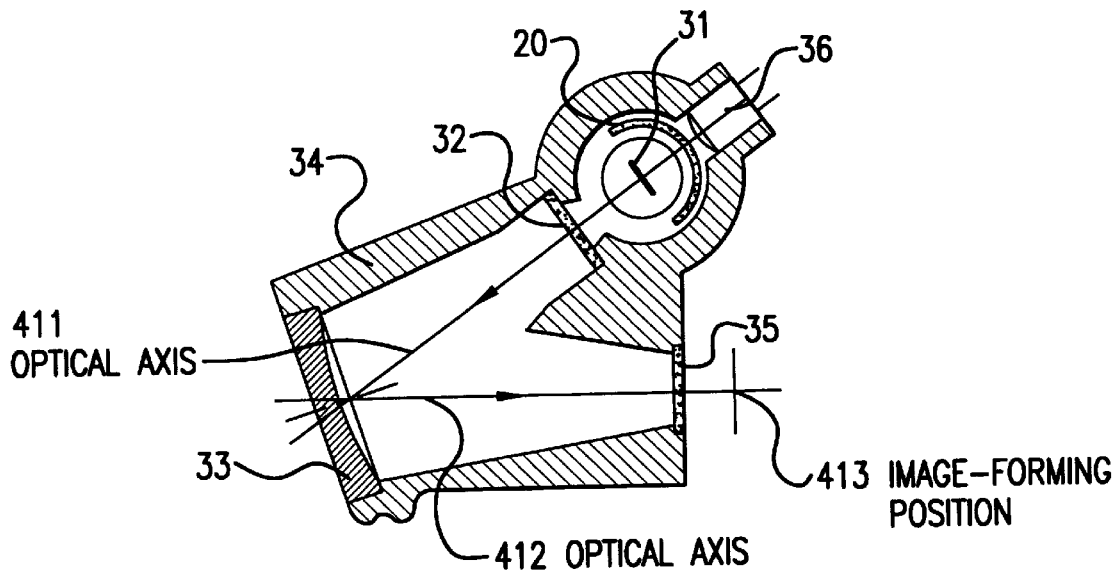
FIG. 4(a) is a cross sectional view showing a locational relationship between the infrared source and a condensing optical system, a direction of an optical axis, and an image-forming position according to the first embodiment.
Figure 4B:
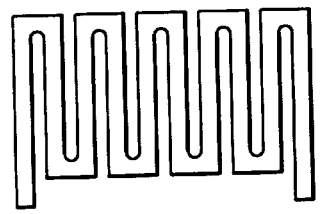
FIG. 4(b) shows an image at the image-forming position.

Next, the condensing optical system is described with reference to FIGS. 4(a) and 4(b). FIG. 4(a) is a cross sectional view showing an optical axis added to the enclosure 34 in FIG. 1. FIG. 4(b) shows a shape of an image formed by the condensing optical system. A part of the infrared flux emitted from the emitter section 31 of the infrared source 30 passes through the infrared transmission window 32, enters along an optical axis 411 onto the concave condensing mirror 33 attached to the enclosure 34 opposite to the infrared transmission window 32, and is reflected and condensed along an optical axis 412 tilted at a predetermined angle relative to the optical axis 411. The flux then passes through the infrared transmission window 35 attached to the enclosure 34 and condensed at an image-forming position 413 to form a zigzag image of the emitter section 31 as shown in FIG. 4(b).

The recessed or concave condensing mirror 33 is a spherical mirror with, for example, a radius of curvature of 50 mm and an aperture of 20 mm; the length of the optical axis 411 joining the emitter section 31 with the recessed condensing mirror 33 is 50 mm; and the recessed condensing mirror 33 is tilted at, for example, 15° relative to the optical axis 411. The image-forming position 413 at which the infrared flux from the emitter section 31 is condensed to form an image is on the optical axis 412 and 50 mm away from the recessed condensing mirror 33.

The image-forming position 413 is designed to align with a position of the image on the incident side of the White cell 70 described below.

The above numerical values are only one example, and the size, arrangement and type of the condensing mirrors such as inclination, radius of curvature, aperture and curved-surface shape (not only a curved surface but also an ellipsoid) of the recessed condensing mirror 33 may vary and be combined arbitrarily.

In addition, since this condensing optical system is sealed by the infrared transmission windows 32 and 35 at the two openings in the enclosure 34 in an air-tight manner, it can also be used as a gas filter by sealing therein a gas that interferes with the detection of a component gas to be analyzed. If the analyzer analyzes, for example carbon monoxide, carbon dioxide is sealed as a gas filter. The function of the gas filter enables the effects of an interfering component to be substantially reduced to allow the concentration to be analyzed more accurately.

Figure 5:
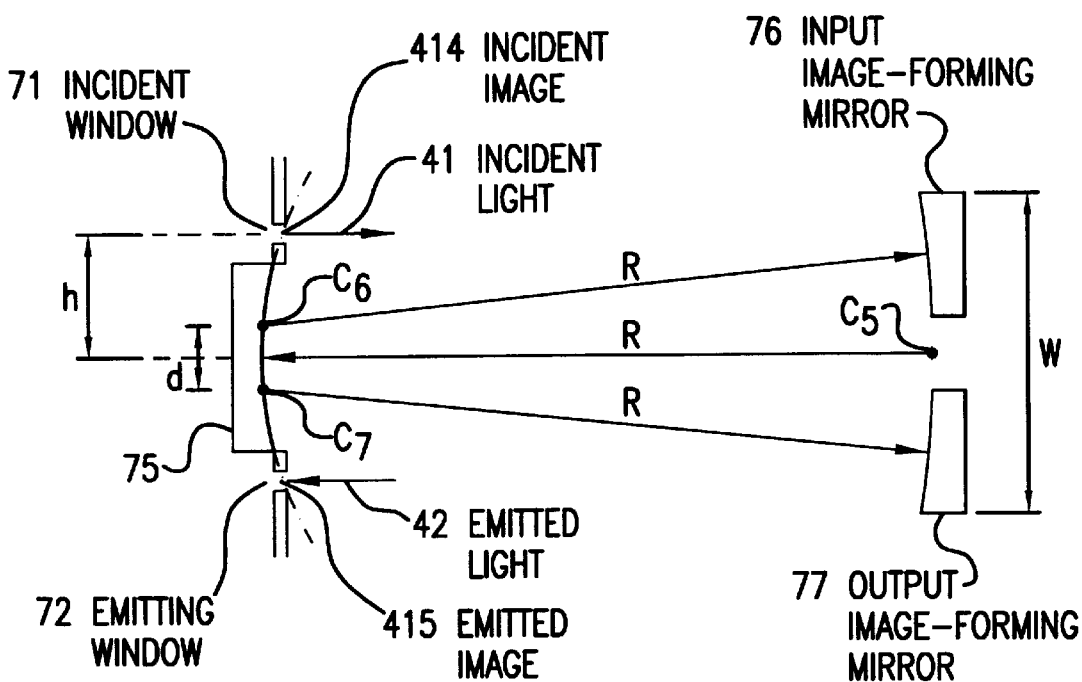
FIG. 5 is a detailed conceptual drawing showing the structure and size of the inside of a White cell according to the first embodiment.
Figure 12:
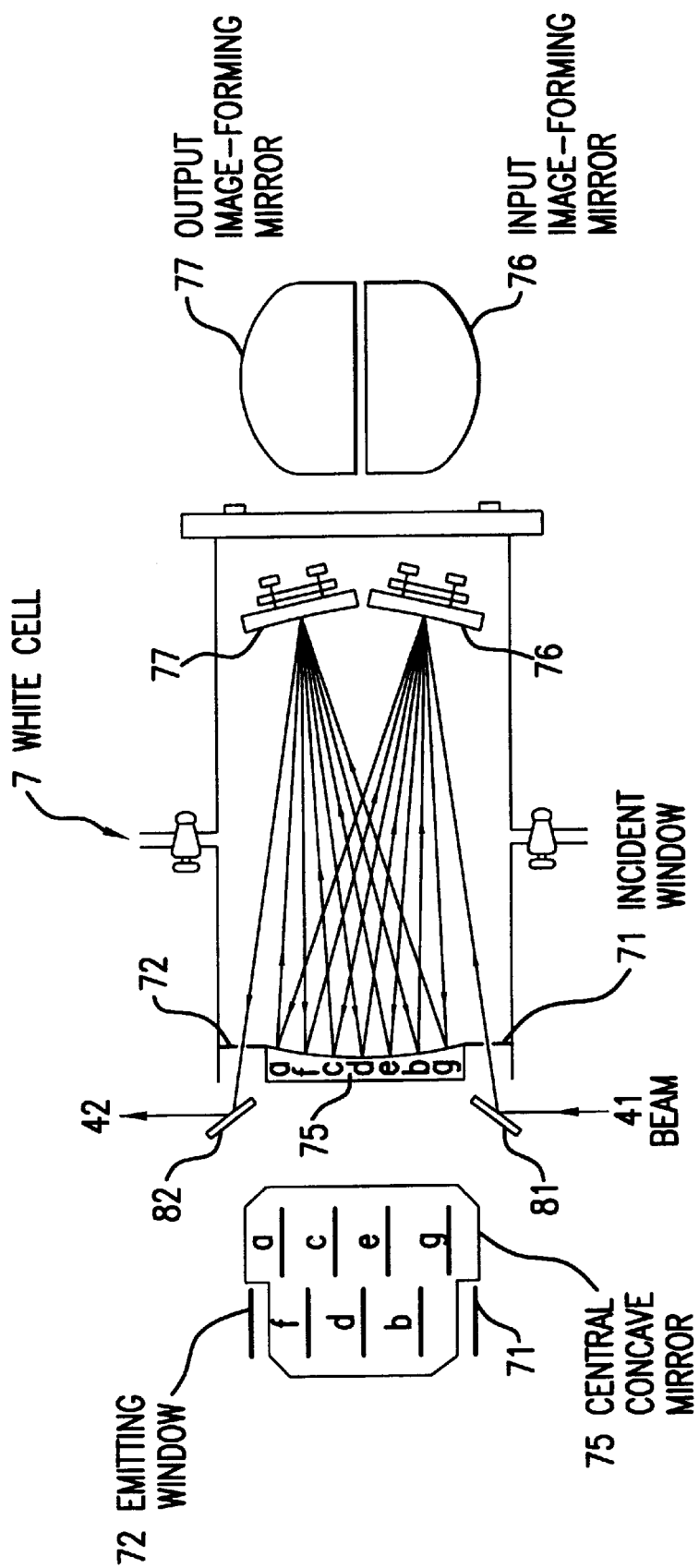
FIG. 12 is a cross sectional view showing the structure of the White cell and the shape of concave reflecting mirrors.

Next, the principle and configuration of the White cell 70 are described with reference to FIG. 5. This is essentially the same as explained in FIG. 12. Three recessed mirrors of the same radius of curvature are an input image-forming mirror 76 opposed to the incident window 71, an output image-forming mirror 77 opposed to the emitting window 72, and a central concave mirror 75 located opposite to these mirrors and between the incident and emitting windows 71 and 72. The distance between an incident image 414 formed at an image-forming position 413 of the input window 71 and the input image-forming mirror 76, the distance between an emitting image 415 on the emitting window 72 and the output image-forming mirror 77, the distance between the input image-forming mirror 76 and the central concave mirror 75, and the distance between the output image-forming mirror 77 and the central concave mirror 75 are set equal to the radius of curvature of the three recessed mirrors. Thus, the incident image 414 is formed on the central recessed mirror 75 by the input image-forming mirror 76, and the reflected image from the central concave mirror 75 is formed again on the central concave mirror 75 by the output image-forming mirror 77. Multiple reflections can be achieved by disposing the three concave mirrors in such a way that the emitting image 415 is formed on the emitting window 72 after a set of two reflection-and-image-forming steps have been repeated for a required number of times.

If the number of reflections inside the White cell 70 is designated by n-1; the radius of curvature of the three concave mirrors is denoted by R; the distance between the center of the incident window 71 and the center of the central concave mirror 75 and the distance between the center of the emitting window 72 and the center of the central concave mirror 75 are each indicated by (h); the distance between the center of curvature of the input image-forming mirror 76 and the center of curvature of the output image-forming mirror 77 is designated by (d); and a required optical path length is denoted by L, then the following relationship is established among these values.

$$R \approx L/n$$

$$h = nd/4$$

((n/2)-1) incident images 414 from the incident window 71 appear on the central concave mirror 75 at the interval (d), and the optical path length within the White cell 70 is obtained four times as large as the radius of curvature R of the concave mirrors.

As an example of designed values for the White cell, if L=500 mm and the number of reflections is 11, the distance between the concave mirrors is about 42 mm, which is about one-tenth of the corresponding distance in a conventional cell.

The assembly of the parts of the White cell 70 and its fixture to the enclosure are carried out through accurate positioning by using parallel pins and fitting operations.

The infrared detector 60 (in FIG. 1) for detecting the concentration of a component gas to be analyzed from infrared rays after travelling over the required optical path length within the White cell 70 has a structure similar to that of the conventional detector 6, but the first and second expansion chambers 63 and 64 can be significantly miniaturized as compared to the prior art because they must only be sized to contain an infrared flux emitted from the White cell 70 therein. This embodiment has been able to reduce the area of the infrared transmission window 61 that captures the infrared rays to one-fourth relative to that of the prior art. The thickness of the heating coil elements 66 and 67 has also been reduced to 1 $\mu$m from a conventional value of 4 $\mu$m in the prior art in order to reduce the heat capacity while improving the heat insulation of the mounting section of the heating coil elements 66 and 67. The sensitivity of the detector 60 has been increased by five times as compared to a conventional detector 6.

The above infrared gas analyzer according to this embodiment has a size of 64×118×117 mm to 64×118×152 mm, so its volume is merely one-tenth or less relative to that of the prior art.

Next, the structure and operation of a single-beam infrared gas analyzer that uses carbon monoxide as a component gas to be analyzed are explained by way of example.

An infrared flux emitted from the infrared source 30 is changed into a discontinuous or intermittent infrared flux of a particular frequency by the rotating chopper 20 that rotates around the emitter section 31. A part of the discontinuous flux that is supplied onto the condensing optical system is condensed by the condensing optical system including the concave condensing mirror 33, in order to form the incident image 414 at the image-forming position 413. Carbon dioxide is sealed in the enclosure 34 of the condensing optical system as a gas filter.

Figure 6:
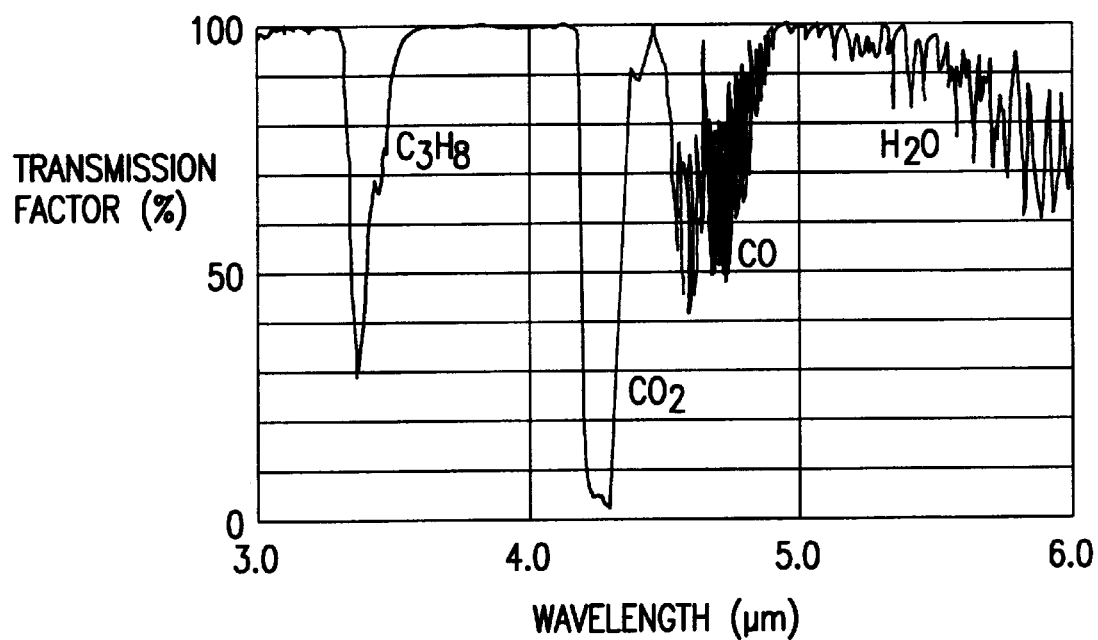
FIG. 6 shows infrared absorption characteristics of various gases.

FIG. 6 shows the transmission factors of infrared rays for carbon monoxide (CO) and carbon dioxide ($CO_2$) at each wavelength. The vertical axis indicates the transmission factor, and the value read from the top of the vertical axis, i.e. 100% as the reference point, toward its bottom indicates the absorption factor for the infrared rays. As is apparent from this figure, the absorbing-wavelength regions of CO and $CO_2$ are close to each other with parts of the absorption ends overlapping each other. $CO_2$ absorbs more infrared rays than CO. In addition, due to its presence in air, $CO_2$ significantly affects infrared rays, so a gas filter must be used to remove infrared rays of a $CO_2$-absorbed region in order to detect low density CO. Thus, $CO_2$ is sealed in the condensing optical system as the gas filter.

The infrared flux free of infrared rays of the $CO_2$-absorbed wavelength region enters the White cell 70, and is repeatedly reflected to pass through the required optical path length. Then, the infrared flux enters the infrared detector 60. The infrared flux entering into the infrared detector 60 has a particular wavelength region absorbed by the analyzing component in the gas to be measured and fed in the White cell 70, in this case, CO depending on its concentration. Thus, the infrared detector 60 with CO sealed therein can detect the amount of infrared rays in a particular wavelength region absorbed from the output corresponding to the amount of infrared rays of a particular wavelength region absorbed by CO in the White cell 70.

Figure 7A:
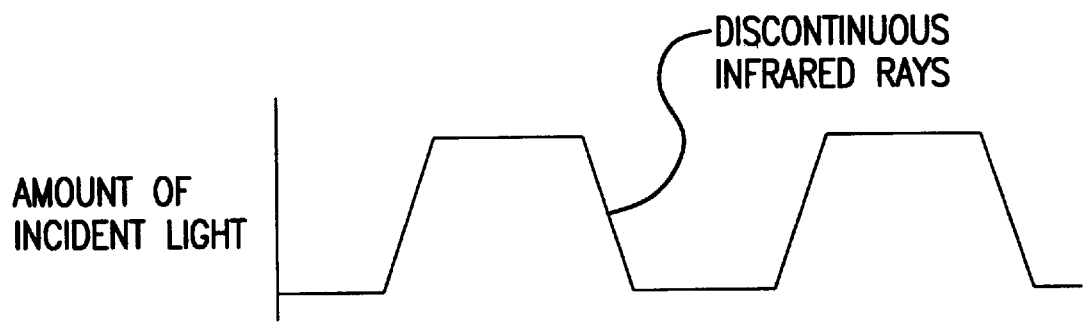
FIG. 7(a) is a chart showing an amount of infrared rays incident on the White cell according to the first embodiment.
Figure 7B:
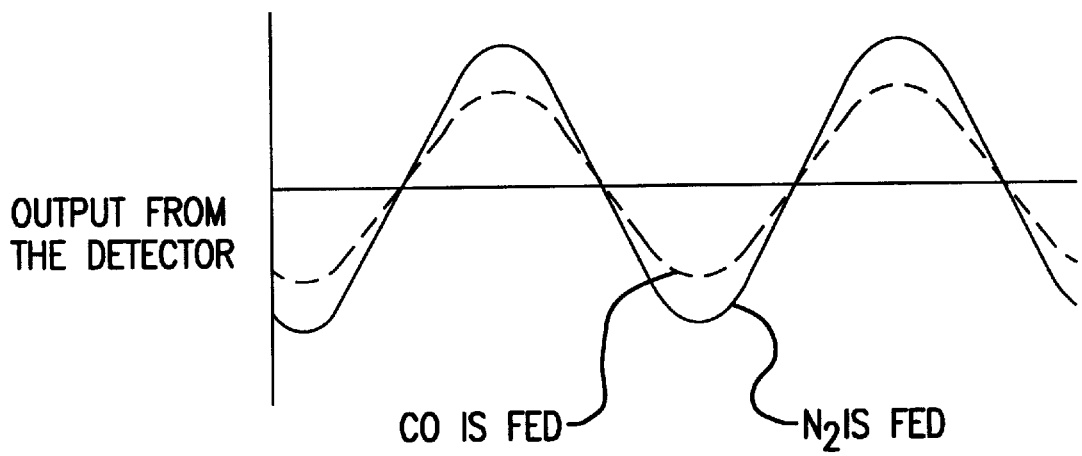
FIG. 7(b) is a chart showing an output from a detector according to the first embodiment.

FIG. 7(a) is a chart showing the amount of incident light measured by the photodiode 36, and FIG. 7(b) is a chart showing the output from the detector 60 with CO sealed therein when CO and nitrogen ($N_2$) are fed in the White cell 70. When $N_2$ was fed, infrared rays of a particular wavelength region were not absorbed in the White cell 70 and a signal with a large amplitude and the same frequency as in chopped discontinuous light was outputted. On the contrary, when CO was fed, infrared rays of a particular wavelength region of 4.5 to 4.9 $\mu$m were absorbed in the White cell 70, and thus a signal with the same frequency and a smaller amplitude was outputted.

The difference in both outputs corresponds to the amount of infrared rays absorbed by CO in the White cell 70. The Lambert-Beer's law shown below is well known in connection with the absorption of infrared rays. That is, if the intensity of incident infrared rays is designated by $I_o$; the intensity of emitted infrared rays is denoted by I; an absorption coefficient specific to a gas is indicated by $\mu$; the concentration of a gas is designated by (c); and the optical path length is denoted by L, then:

$$I = I_o \exp(-\mu c L)$$

As seen in this relational expression, $I_o, \mu$, c and L are known values in the infrared gas analyzer according to this embodiment, so the concentration of the gas can be determined by measuring the changes in the intensity of emitted infrared rays I by using the infrared detector 60.

Although it is usually difficult to obtain the required sensitivity due to a decrease in the usage efficiency of infrared rays when the condensing optical system is used, this embodiment uses as the emitter element 311 of the infrared source 30 a ceramic emitter such as molybdenum silicide that can be used at much higher temperatures than the conventional sources of light. This reduces the thickness of the heating coil elements 66 and 67 of the infrared detector 60, and improves the detector's sensitivity, to thereby obtain a performance equal to or higher than that of the conventional infrared gas analyzers.

In this manner, the first problem is solved by reducing the volume of the analyzer to a fraction of the volume required by the prior art. The second and third problems are solved by entirely miniaturizing and forming the analyzer so as to eliminate the air layer in the connections between the components, attaching optical components such as concave mirrors to the enclosure, and thermally, integrally and tightly assembling each enclosure to maintain a uniform temperature across the entire analyzer in order to prevent the optical axis from being displaced due to thermal expansion.

Although this embodiment seals the particular gas in the condensing optical system to also function as a gas filter, this function is not required when analyzing a high density gas or if there is only a small amount of an interfering component.

A second embodiment is explained with reference to FIGS. 8(a), 8(b), 9(a) and 9(b).

Figure 8A:
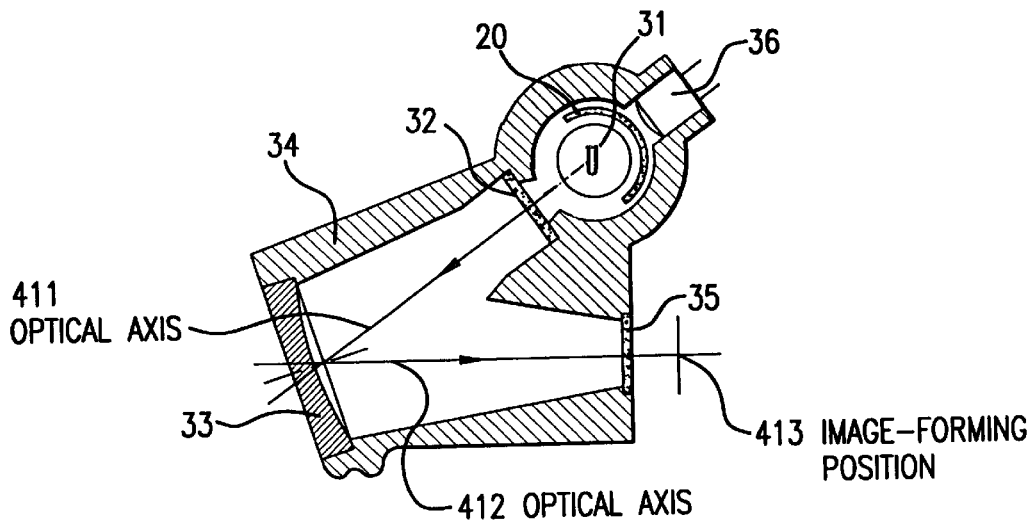
FIG. 8(a) is a cross sectional view showing a locational relationship between an infrared source and a condensing optical system, a direction of the optical system, and an image-forming position according to a second embodiment of the invention.
Figure 8B:
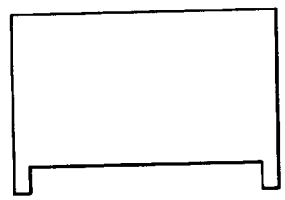
FIG. 8(b) shows an image at the image-forming position.
Figures 9A, 9B:
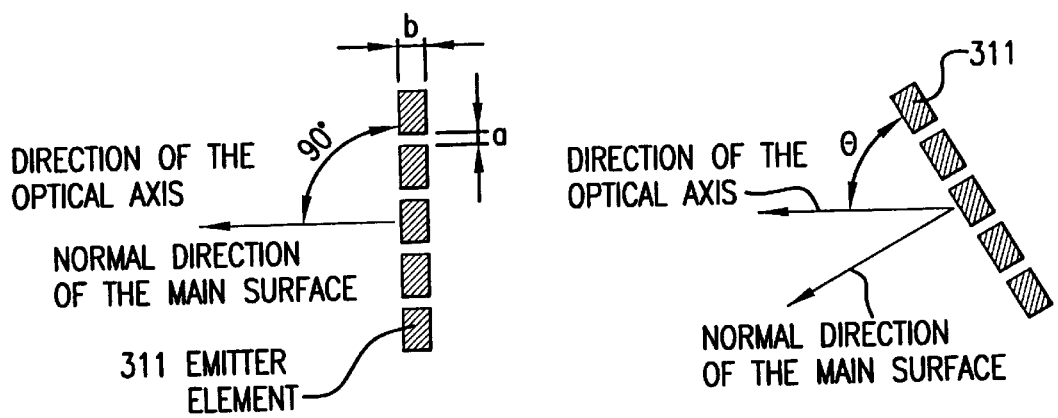
FIG. 9(a) shows a relationship between the direction of the optical axis and the normal direction of the main surface of the emitter element according to the first embodiments.
FIG. 9(b) shows a relationship between the direction of the optical axis and the normal direction of the main surface of the emitter element according to the second embodiment.
Figure 10:
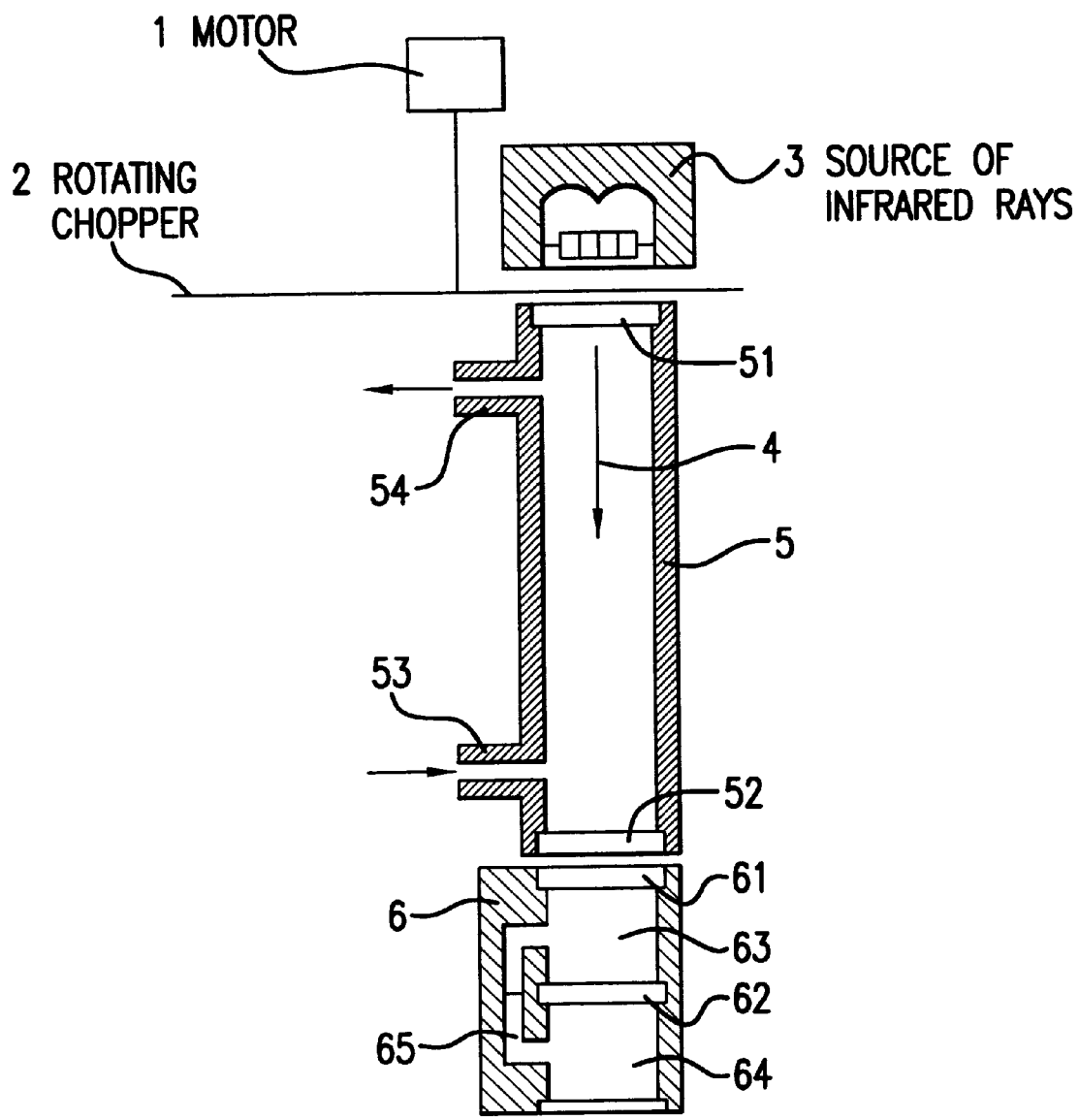
FIG. 10 is a cross-sectional view showing a structure of a conventional infrared gas analyzer.

FIG. 8(a) is a cross sectional view showing the relationship between the direction of the emitter section 31 in the enclosure 34 and the optical axis 411, and FIG. 8(b) shows a shape of an image at the image-forming position 413 in FIG. 8(a). FIGS. 9(a) and 9(b) show enlarged views of the emitter elements 311 for comparing the first embodiment and the second embodiment, wherein FIG. 9(a) illustrates the first embodiment, and FIG. 9(b) illustrates the second embodiment.

According to the first embodiment, the normal direction of the main surface of the emitter element 311 is aligned with the direction of the optical axis 411, and the zigzag shape of the emitter section as shown in FIG. 4(b) directly appears at the image-forming position 413. In the second embodiment, however, the normal direction of the main surface of the emitter element 311 is tilted relative to the direction of the optical axis 411, and an image of a surface light source indicating the outer circumference of the emitter section as shown in FIG. 8(b) appears at the image-forming position 413 and the actual image is slightly larger than the enveloped area in FIG. 4(b). This is because the optical axis 411 is tilted relative to the normal direction of the main surface to expose the side of the emitter element 311 in the thickness direction while concealing the gaps between the zigzag emitters. By tilting the direction of the emitter section relative to the optical axis 411 in this manner, the same emitter elements 311 can be used to obtain a larger amount of infrared flux.

As shown in FIG. 9(a), if the gap between the adjacent emitter sections is designated by (a) and the thickness of the emitter is indicated by (b), the gaps between the emitter sections are concealed when the angle θ of the optical axis 411 relative to the main surface of the emitter element 311 meets the following condition.

$$\tan\theta \leq (b/a)$$

In addition, the exposed area of the emitter is maximum when the optical axis 411 is set perpendicular to the diagonal direction of the individual cross sections of the emitter element 311. By setting θ at the value of the above angle, that is, adjusting (a) relative to (b), the emitter can be used most efficiently.

Thus, to efficiently use this example, the emitter must have a certain thickness and the projecting area of the emitter as tilted must be larger than that as seen from the front, and the ceramic emitter consisting of molybdenum silicide described in the first embodiment is optimal in implementing this invention.

According to the first aspect of the invention, an infrared gas analyzer comprises a source of infrared rays for emitting infrared rays; infrared flux interrupting means for chopping an emitted infrared flux; a condensing optical system for obtaining a predetermined solid angle in the emitted infrared flux to thereby form a condensed flux; a multiple reflection cell disposed at an outlet of the condensing optical system, to which the condensed flux is ejected and a gas to be measured is fed, the multiple reflection cell having a built-in multiple reflection optical system composed of three concave mirrors; and infrared amount detection means disposed at an infrared emitting section of the multiple reflection cell for detecting an amount of infrared rays with a wavelength band absorbed by a component gas to be analyzed and contained in the infrared rays emitted by the multiple reflection cell, wherein at least the condensing optical system, multiple reflection cell and infrared amount detecting means are accurately positioned by using as a reference a position of the condensing optical system at which the condensed flux is emitted and are coupled tightly at coupling positions without an air-flowing layer. Thus, the entire analyzer can be substantially miniaturized and thermally integrally formed to provide an accurate optical path for the infrared rays and to enable the multiple reflection cell to function effectively, thereby enabling a low density analyzing-component gas to be detected and analyzed. Therefore, the invention can provide a small infrared gas analyzer that can detect and analyze a low density analyzing-component gas and that can be used in an explosion-proof environment.

According to the second aspect of the invention, the condensing optical system and the infrared amount detector are contacted with each other to maintain a uniform temperature. This configuration can maintain a uniform temperature of the entire analyzer to thereby provide a smaller and more stable infrared gas analyzer.

According to the third aspect of the invention, the analyzer includes as an infrared radiating section of the infrared source an emitter comprising molybdenum silicide or a composite ceramic containing molybdenum silicide, thereby allowing the operating temperature of the emitter to be significantly increased. Therefore, this invention can provide a small and high-power infrared source.

According to the fourth aspect of the invention, a holding section of the infrared radiating section of the infrared source includes a hermetic structure, thereby enabling the emitter to be positioned accurately. Thus, the infrared flux can be accurately condensed at the image-forming position, and enables the White cell to function efficiently.

According to the fifth aspect of the invention, the infrared radiating section of the infrared source is shaped by folding or bending a ribbon with a rectangular cross section. The thickness of the ribbon and the interval between the folded parts of the ribbon is almost equal, and the direction perpendicular to the main emitting surface of the infrared radiating section is tilted relative to the incident axis of the condensing optical system. Thus, not only infrared rays from the main radiating surface of the infrared radiating section but also infrared rays from the sides can be used to increase the effective infrared radiating area. This can in turn increase the amount of infrared rays supplied to the White cell by the infrared source. This increases the output of the detector and thus the sensitivity of the infrared gas analyzer.

According to the sixth aspect of the invention, the infrared flux interrupting means is formed by cutting a part of a cylinder and mounting a shaft at the center of one end of the cylinder in such a way that the shaft can be rotated, and the infrared flux interrupting means covers the infrared radiating section of the infrared source so as to rotate around the infrared radiating section. Thus, the infrared flux interrupting means can be substantially miniaturized as compared to the conventional disc methods and integrally incorporated in the infrared source section with ease, thereby facilitating the miniaturization and integration of the infrared gas analyzer.

According to the seventh aspect of the invention, a particular component gas is sealed inside the condensing optical system and the condensing optical system also functions as a gas filter. This configuration can eliminate the effects of an interfering-component gas to stabilize the performance of the infrared detector, thereby providing a very sensitive infrared gas analyzer.

According to the eighth aspect of the invention, a photo detector is disposed so that a part of the infrared flux from the infrared source which is chopped by the infrared flux interrupting means can be detected. This configuration enables the conditions of the infrared source and infrared flux interrupting means to be detected. Thus, it is possible to detect an error therein or to compensate for the sensitivity of the infrared detector, thereby improving the reliability of the infrared gas analyzer and its detection accuracy.

According to the ninth aspect of the invention, the rotational condition of the infrared flux interrupting means is detected by using the chopping frequency of the infrared source detected by the photo detector. This configuration enables an error in the rotation of the infrared flux interrupting means, e.g. its stoppage, to be detected, thereby enhancing the reliability of the infrared gas analyzer.

According to the tenth aspect of the invention, an amount of light from the infrared source is calculated from the output from the photo detector. This makes it possible to detect the nature of changes in the characteristics of the infrared source and to correct the variation of voltages applied to the infrared source and infrared amount detector. In this way, the sensitivity of the infrared level detector can be adjusted. This configuration can significantly improve the stability of the sensitivity of the infrared amount detection means and the detection accuracy of the infrared gas analyzer.

According to the eleventh aspect of the invention, the output from the photo detector is used as a reference signal for a processing circuit for the infrared amount detector. This configuration significantly improves the accuracy of processing executed by the processing circuit for the infrared amount detection means, thereby providing a very sensitive infrared gas analyzer.

What is claimed is:

1. An infrared gas analyzer comprising:
    a source of infrared rays for emitting infrared flux, said source of the infrared rays having an emitter formed of a material selected from the group consisting of molybdenum silicide and a composite ceramic containing molybdenum silicide;
    an infrared flux interrupting device situated near the source of the infrared rays for chopping the emitted infrared flux from the source of the infrared rays;
    a condensing optical system situated near the infrared flux interrupting device for obtaining a predetermined solid angle in the emitted infrared flux to thereby form a condensed flux, said condensing optical system having an outlet;
    a multi-reflection cell disposed at the outlet of the condensing optical system, to which the condensed flux is supplied and a gas to be measured is fed, said multi-reflection cell having an infrared emitting section and a multi-reflection optical system formed of a plurality of concave mirrors; and
    an infrared level detector disposed at the infrared emitting section of the multi-reflection cell for detecting an amount of infrared rays with a wavelength band absorbed by a component gas to be analyzed and contained in the infrared rays emitted by the multi-reflection cell, at least said condensing optical system, multi-reflection cell and infrared level detector being accurately positioned by using as a reference a position of the condensing optical system at which the condensed flux is emitted, and being coupled tightly at coupling positions without an air-flowing layer.

2. An infrared gas analyzer according to claim 1, wherein said condensing optical system and the infrared level detector contact each other to maintain a uniform temperature therebetween.

3. An infrared gas analyzer according to claim 1, wherein said source of the infrared rays includes a holding section having a hermetic structure.

4. An infrared gas analyzer according to claim 1, further comprising a photo detector disposed adjacent to the source of the infrared rays so that a part of the infrared flux chopped by the infrared flux interrupting device is detected.

5. An infrared gas analyzer according to claim 4, wherein said photo detector detects a rotational condition of the infrared flux interrupting device through a chopping frequency of the infrared source.

6. An infrared gas analyzer according to claim 4, wherein said photo detector calculates an amount of light from the source to detect a condition of changes in characteristics of the source, and corrects a variation of voltages applied to the source and said infrared level detector to adjust a sensitivity of the infrared level detector.

7. An infrared gas analyzer according to claim 4, wherein said photo detector provides an output used as a reference signal for a processing circuit for an infrared level detector.

8. An infrared gas analyzer according to claim 1, wherein said multi-reflection optical system is formed of three concave mirrors.

9. An infrared gas analyzer comprising:
    a source of infrared rays for emitting infrared flux, said source of the infrared rays having an infrared radiating section formed of a bent ribbon with a rectangular cross section, the thickness of the ribbon and an interval between bent parts of the ribbon being substantially equal;
    an infrared flux interrupting device situated near the source of the infrared rays for chopping the emitted infrared flux from the source of the infrared rays;
    a condensing optical system situated near the infrared flux interrupting device for obtaining a predetermined solid angle in the emitted infrared flux to thereby form a condensed flux and having an outlet, a direction perpendicular to a main emitting surface of the infrared radiating section being tilted relative to an incident axis of the condensing optical system;
    a multi-reflection cell disposed at the outlet of the condensing optical system, to which the condensed flux is supplied and a gas to be measured is fed, said multi-reflection cell having an infrared emitting section and a multi-reflection optical system formed of a plurality of concave mirrors; and an infrared level detector disposed at the infrared emitting section of the multi-reflection cell for detecting an amount of infrared rays with a wavelength band absorbed by a component gas to be analyzed and contained in the infrared rays emitted by the multi-reflection cell, at least said condensing optical system, multi-reflection cell and infrared level detector being accurately positioned by using as a reference a position of the condensing optical system at which the condensed flux is emitted, and being coupled tightly at coupling positions without an air-flowing layer.

10. An infrared gas analyzer comprising:

a source of infrared rays for emitting infrared flux;

an infrared flux interrupting device situated near the source of the infrared rays for chopping the emitted infrared flux from the source of the infrared rays, said infrared flux interrupting device having a cylinder, a cutting part formed in the cylinder and a shaft formed at a center of one end of the cylinder such that the shaft is rotated, said infrared flux interrupting device covering an infrared radiating section of the infrared source and rotating around the infrared radiating section;

a condensing optical system situated near the infrared flux interrupting device for obtaining a predetermined solid angle in the emitted infrared flux to thereby form a condensed flux, said condensing optical system having an outlet;

a multi-reflection cell disposed at the outlet of the condensing optical system, to which the condensed flux is supplied and a gas to be measured is fed, said multi-reflection cell having an infrared emitting section and a multi-reflection optical system formed of a plurality of concave mirrors; and an infrared level detector disposed at the infrared emitting section of the multi-reflection cell for detecting an amount of infrared rays with a wavelength band absorbed by a component gas to be analyzed and contained in the infrared rays emitted by the multi-reflection cell, at least said condensing optical system, multi-reflection cell and infrared level detector being accurately positioned by using as a reference a position of the condensing optical system at which the condensed flux is emitted, and being coupled tightly at coupling positions without an air-flowing layer.

11. An infrared gas analyzer comprising:

a source of infrared rays for emitting infrared flux;

an infrared flux interrupting device situated near the source of the infrared rays for chopping the emitted infrared flux from the source of the infrared rays;

a condensing optical system situated near the infrared flux interrupting device for obtaining a predetermined solid angle in the emitted infrared flux to thereby form a condensed flux, said condensing optical system having an outlet and containing a predetermined component gas sealed therein to function as a gas filter;

a multi-reflection cell disposed at the outlet of the condensing optical system, to which the condensed flux is supplied and a gas to be measured is fed, said multi-reflection cell having an infrared emitting section and a multi-reflection optical system formed of a plurality of concave mirrors; and an infrared level detector disposed at the infrared emitting section of the multi-reflection cell for detecting an amount of infrared rays with a wavelength band absorbed by a component gas to be analyzed and contained in the infrared rays emitted by the multi-reflection cell, at least said condensing optical system, multi-reflection cell and infrared level detector being accurately positioned by using as a reference a position of the condensing optical system at which the condensed flux is emitted, and being coupled tightly at coupling positions without an air-flowing layer.

* * * * *